United States Patent [19]
Hakalehto

[11] Patent Number: 5,846,209
[45] Date of Patent: Dec. 8, 1998

[54] SYRINGE COMPRISING AN ADHERING SUBSTRATE FOR MICROBES

[76] Inventor: Elias Hakalehto, Kasarmikatu 12 C 1, FIN-70110 Kuopio, Finland

[21] Appl. No.: 765,744
[22] PCT Filed: Jul. 10, 1995
[86] PCT No.: PCT/FI95/00398
    § 371 Date: Feb. 24, 1997
    § 102(e) Date: Feb. 24, 1997
[87] PCT Pub. No.: WO96/01890
    PCT Pub. Date: Jan. 25, 1996

[30] Foreign Application Priority Data

Jul. 11, 1994 [FI] Finland ................................. U940376

[51] Int. Cl.[6] ....................................................... A61B 5/00
[52] U.S. Cl. ............................................ 600/572; 600/584
[58] Field of Search ................................. 600/562, 569, 600/572, 573, 584

[56] References Cited

U.S. PATENT DOCUMENTS

| | | | |
|---|---|---|---|
| 3,450,129 | 6/1969 | Avery . | |
| 4,164,212 | 8/1979 | Schuster | 600/572 |
| 4,252,904 | 2/1981 | Nelson et al. | 435/294 |
| 4,784,158 | 11/1988 | Okinoto | 600/572 |
| 4,960,130 | 10/1990 | Guirguis | 600/584 |
| 5,339,828 | 8/1994 | Keating et al. | 600/572 |
| 5,339,829 | 8/1994 | Thieme et al. | 600/584 |
| 5,477,863 | 12/1995 | Grant | 600/572 |

FOREIGN PATENT DOCUMENTS 0 058 008  8/1982  European Pat. Off. .

*Primary Examiner*—Max Hindenburg
*Attorney, Agent, or Firm*—Young & Thompson

[57] ABSTRACT

A syringe, preferably an injector syringe, comprises a cylindrical receiver (1') and inside its plunger device (2') comprising a plunger (3') and a rod (4'). In order for the syringe to simplify taking and handling microbiological sweep samples, the syringe is characterized in that the surface facing away from the plunger (3') rod (4') comprises an adhering substrate (6') for microbes. The adhering substrate (6') is preferably arranged to a member (7'), detachably attachable to the plunger (3').

10 Claims, 2 Drawing Sheets

SYRINGE COMPRISING AN ADHERING SUBSTRATE FOR MICROBES

FIELD OF THE INVENTION

The invention relates to a syringe, preferably an injector syringe, the syringe comprising a cylindrical receiver and inside it plunger means comprising a plunger and a rod.

BACKGROUND OF THE INVENTION

Collecting microbiological sweep samples is an important part of hygiene control in industrial establishments, hospitals, laboratories and other places where the hygiene of the premises, apparatuses and equipment is an absolute operational prerequisite. Sweep samples may also be collected from e.g. human skin or mucous membranes for clinical diagnostics.

Samples may alternatively be taken by picking. In further processing of microbiological samples, a sample may be taken, e.g. from a culture substrate, such as a Petri dish, of microbial colonies by picking a colony into proper sampling means, such as a cotton swab.

Usually a microbiological sweep sample or a picked sample is suspended from sampling means into a buffer solution or any other appropriate solution, where it may be further examined and handled. In this case a usual method for acquiring additional information on possible microbes adhered to the sampling means is so-called subculture. This is usually accomplished by transferring the microbial suspension to be examined to a liquid culture substrate or to a solid culture substrate (e.g. a Petri dish). Thereafter the microbes in the culture substrate are incubated for at least some hours, but usually for one or more days, even weeks.

In some situations rapid completion of a microbiological analysis is crucially important e.g. for the success of a patient's treatment, in choosing cleansing measures in hygiene control, for industrial quality control etc. Many factors have further increased the threat caused by microbes (hospital infections, new human and animal pathogens, previously unknown industrial microbial contaminants, environmental microbiological pollution etc.). In order to be able to respond to these challenges adequately effectively, so-called rapid diagnostic methods are needed for indicating and identifying microbes.

For effecting microbiological rapid tests, several methods have been developed based on e.g. genetic analysis or immunodiagnosis. The expression "rapid test" in its proper sense refers to a method not requiring a time-consuming culture of microbes for enriching them in a sample (pre-incubation). In many practical situations rapid tests have to be used whereat the samples to be examined often have an extremely low content of microbial cells.

SUMMARY OF THE INVENTION

The object of the present invention is to provide an apparatus for taking microbiological sweep samples, the apparatus allowing an extremely simple transfer of microbes into a suspending solution, from where the microbes may be gathered by filtration (enrichment without microbial culture) and further processed for an immunological determination in a manner described in Finnish Patent Application 924,834. The apparatus of the invention may also be used with methods where microbes are cultivated. By swinging the apparatus as a test tube, its contents may be treated, which is one manner of operating the apparatus of the invention.

The above objects are achieved with the syringe of the invention, which is characterized in that the surface facing away from the plunger rod comprises an adhering substrate for microbes. The adhering substrate is preferably of cotton. It is also preferable that the adhering substrate is arranged onto means detachably attachable to the plunger, as such an adhering substrate is easily replaceable and the adhering surface may be arranged to suit different purposes of use. This decreases work and working phases in sampling. It is also possible to suspend the sample in the same means where the sample is being transferred, which is preferable especially when hazardous microbes are handled.

The preferable embodiments of the invention are described in the attached claims 2 through 10.

The invention is based on the realization that the plunger of a conventional manual syringe may be used as sampling means, wherefore the surface of the plunger is appropriately treated so as to make microbes adhere thereto, whereat the receiver of the syringe is used for performing suspending for detaching the microbes and the suspending solution may be transferred in the syringe to a desired destination.

The main advantages of the syringe of the invention are that it considerably simplifies taking and handling microbiological sweep samples.

BRIEF DESCRIPTION OF THE INVENTION

In the following the invention will be described by way of working examples with reference to the accompanying drawings, in which FIG. 1 shows a first embodiment of a syringe of the invention disassembled, FIGS. 2 through 4 illustrate the use of the syringe of FIG. 1, FIG. 5 shows a second embodiment of a syringe of the invention disassembled, FIG. 6 shows the plunger of an embodiment of the invention, FIG. 7 shows an embodiment of a syringe of the invention disassembled, and FIG. 8 shows the plunger of an embodiment of the invention.

DETAILED DESCRIPTION OF THE INVENTION

Figure 1:
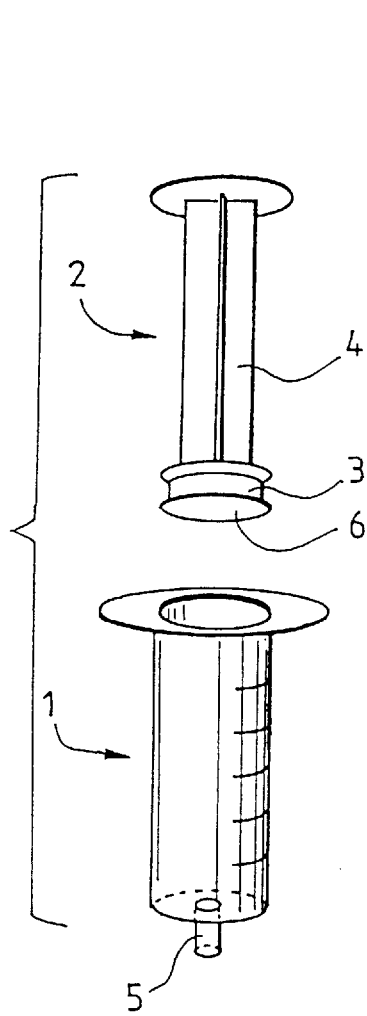

FIG. 1 shows a manual injector-type syringe for taking microbiological sweep samples, comprising a conventional cylindrical receiver 1 and therein mountable plunger means 2 comprising a plunger 3 and a rod 4. The receiver 1 extends in a longitudinal axis from a first end to an opposite second end a first distance. The surface facing away from the rod 4 of the plunger 3, i.e. the surface facing the tip 5 of the receiver 1, comprises a cotton layer 6. The cotton layer 6 functions by adhering microbes thereto. Instead of a cotton layer, the surface of the plunger 3 may be of velvet, porous, moistened paper or other corresponding material, whereto microbes easily adhere. The materials form thus an adhering substrate for microbes. It is feasible that a roughened surface may alternatively be used as an adhering substrate, whereat the surface facing the tip 5 of the plunger 3 is thus roughened. Furthermore, said adhering substrate may be a surface treated with chemicals to effect adhering. The plunger 3 has a first surface facing the rod 4 and an opposite second surface facing away from the rod. The adhering substrate 6 is attached to the second surface, and extends away from the second surface to an adhering substrate surface a second distance. The second distance is substantially smaller than the first distance.

Figure 2:
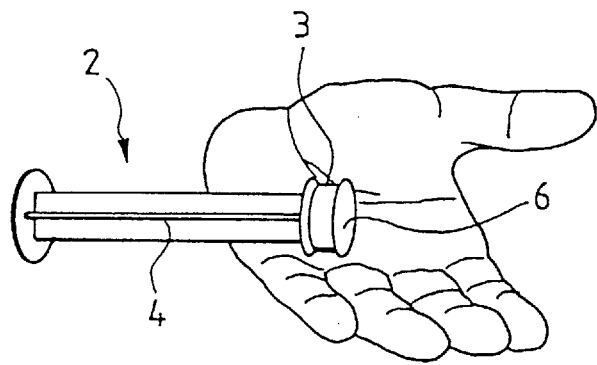
Figure 3:
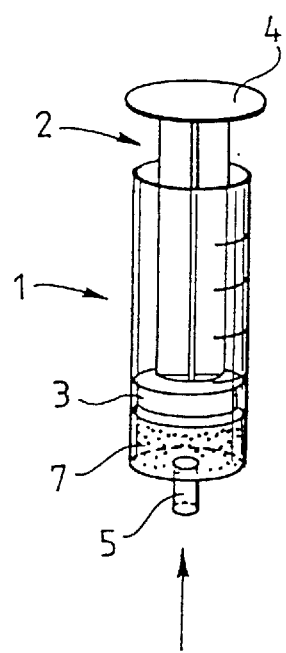
Figure 4:
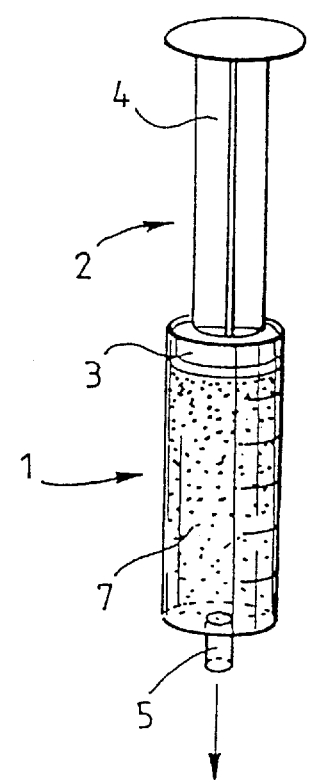

When the syringe of FIG. 1 is used for taking microbiological sweep samples, the procedure is as shown in FIG. 2. According to FIG. 2, the plunger means 2 is brought into contact with a hand, from which a sample is desired to be taken. When sampling, the cotton layer 6 of the plunger means 2 is swept to and fro on the surface of the hand, whereat microbes adhere to the cotton layer. Thereafter the plunger means 2 is placed in an empty receiver 1 and the receiver is filled with suspending solution 7 by suction, see FIG. 3. During suspending the microbial cells are detached from the cotton layer 6. If desired, the detachment may be intensified by pulling the sample to and fro several times between the syringe and the receiver. Thereafter the microbes in the solution may be transferred e.g. to a filter and thereafter treated for immunological analysis.

Figure 5:
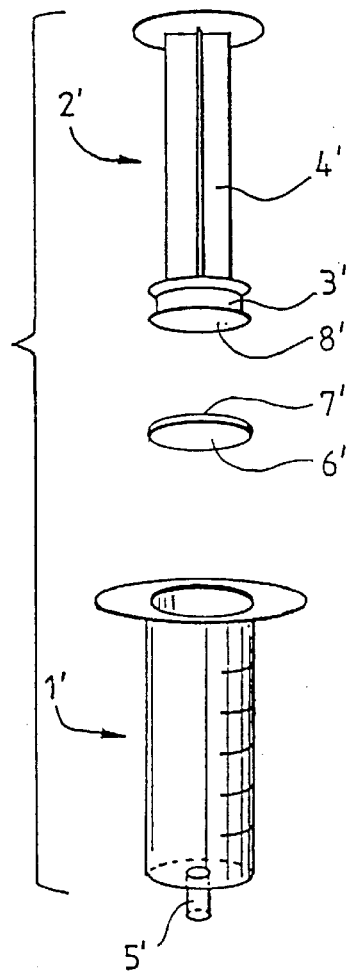

The embodiment of FIG. 5 differs from that of FIG. 1 in that is comprises a disciform member 7', detachably attached to a plunger 3', said member comprising an adhering substrate 6'. The surface of the member 7' preferably corresponds to the area of the plunger 3'. In order for the member to be attachable to and detachable from the plunger 3', one of its surfaces is adhesive. Alternatively it may comprise sticker fastening means cooperating with the surface 8' of the plunger.

Figure 6:
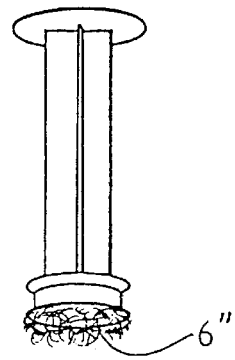

The plunger shown in FIG. 6 comprises cotton 6" as an adhering substrate.

Figure 7:
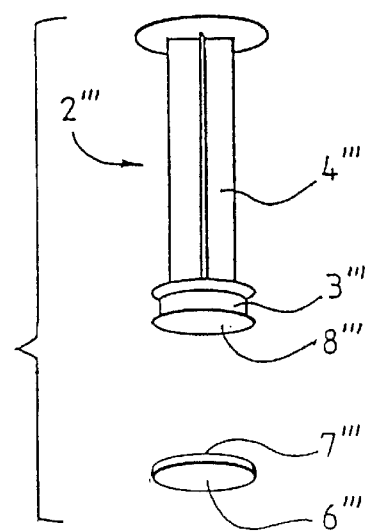

FIG. 7 shows an embodiment of the invention, where an adhering substrate is arranged in a planar disciform member 7''', attachable by sticker means to a plunger 3''', whereat the plunger comprises a corresponding surface 8''', needed for sticker fastening.

Figure 8:
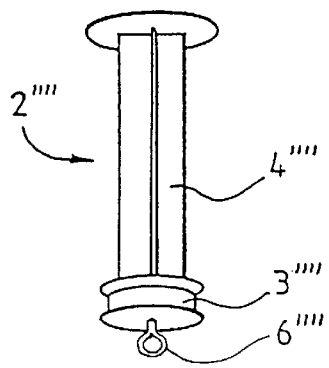

FIG. 8 illustrates an embodiment of the invention, where the end of a plunger 3"" comprises a projection 6"", functioning as an adhering substrate. Such a plunger 3"" may be used when samples are picked from microbial colonies. The projection 6"" may be in the form of a loop, as in the Figure, and it may be of a flexible type. The projection 6"" may be arranged to be relatively easily detachable from the surface of the plunger 3"", when desired. This may be accomplished by manufacturing the projection from an appropriate material and by arranging the fastening to the plunger to be of a certain fastness. It is also feasible that the projection is of a transparent material.

Although the invention is described herein with reference to examples it will be appreciated that the details of the invention may be realized in a variety of ways within the scope of the inventive idea and the appended claims. Thus the detailed structure, shape and size of the syringe may vary. It is feasible that the syringe forms a structural part of a larger apparatus, designed for handling and analysing microbial samples.

I claim:

1. A syringe for collecting microbiological sweep samples, comprising slideably engaging receiver and plunger means, said receiver extending in a longitudinal axis from a first end to an opposite second end a first distance, said plunger means comprising an elongated rod and a plunger attached to said rod, said plunger having a first surface facing said rod and an opposite second surface facing away from said rod, and an adhering substrate attached to said second surface, said substrate extending away from said second surface to an adhering substrate surface a second distance, said second distance being substantially smaller than said first distance.

2. The syringe according to claim 1, wherein the adhering substrate is of cotton.

3. The syringe according to claim 1, wherein the adhering substrate is of velvet.

4. The syringe according to claim 1, wherein the adhering substrate is of porous paper.

5. The syringe according to claim 1, wherein the adhering substrate is a roughened surface.

6. The syringe according to claim 1, wherein the adhering substrate is a chemically treated surface for adhering microbes.

7. The syringe according to claim 1, wherein the adhering substrate is arranged in a member which is detachably attachable to the plunger.

8. The syringe according to claim 7, wherein the member is a planar member having an adhesive surface.

9. The syringe according to claim 7, wherein the member is a planar member attachable by sticker means to the second surface.

10. The syringe according to claim 1, wherein the adhering substrate is in the form of a projection.

\* \* \* \* \*